United States Patent [19]

Ruoslahti

[11] Patent Number: 5,498,694
[45] Date of Patent: Mar. 12, 1996

[54] PEPTIDES OF THE CYTOPLASMIC DOMAIN OF INTEGRIN

[75] Inventor: Erkki I. Ruoslahti, Rancho Santa Fe, Calif.

[73] Assignee: La Jolla Cancer Research Foundation, La Jolla, Calif.

[21] Appl. No.: 240,967

[22] Filed: May 10, 1994

Related U.S. Application Data

[63] Continuation of Ser. No. 973,547, Nov. 9, 1992, abandoned, which is a continuation of Ser. No. 357,024, May 25, 1989, abandoned.

[51] Int. Cl.$^6$ .............................. C07K 7/08; C07K 14/00
[52] U.S. Cl. ........................ 530/324; 530/326; 530/327; 530/806
[58] Field of Search .................................. 530/324, 326, 530/327, 806

[56] References Cited

U.S. PATENT DOCUMENTS 4,722,899  2/1988  Hamaoka et al. .................... 435/172.2

OTHER PUBLICATIONS

Seaver, Genetic Engineering News, pp. 10 and 21 (1994).
Coombs, Dictionary of Biotechnology, Elsevier Science Publishing Co., Inc. New York, pp. 312 and 120 (1986).
Harlow et al., Antibodies, A Laboratory Manual, Cold Spring Harbor Laboratory, p. 98 (1988).
Rudinger, Peptide Hormones Parsons, (Ed.), U. Park Press, Baltimore, pp. 1–7 (1976).
Marcantonio, E. E. and Hynes, R. O., Antibodies to the Conserved Cytoplasmic Domain of the Integrin B$_1$ Subunit React with Proteins in Vertebrates, Invertebrates, and Fungi, The Journal of Cell Biology 106:1765–1772 (1988).
Ruoslahti, E. and Pierschbacher, M. D., New Perspectives in Cell Adhesion: RGD and Integrins, Science 238:491–497 (1987).
Argraves et al., Amino Acid Sequence of the Human Fibronectin Receptor, The Journal of Cell Biology 105:1183–1190 (1987).
C. H. Damsky et al., Distribution of the Cell Substratum Attachment (CSAT) Antigen on Myogenic and Fibroblastic Cells in Culture, The Journal of Cell Biology 100:1528–1539 (1985).
W. Chen et al., Development of Cell Surface Linkage Complexes in Cultured Fibroblasts, The Journal of Cell Biology 100:1103–1114 (1985).
E. Dejana et al., Fibronectin and Vitronectin Regulate the Organization of Their Respective Arg–Gly–Asp Adhesion Receptors in Cultured Human Endothelial Cells, The Journal of Cell Biology 107:1215–1223 (1988).
P. Burn et al., Dynamic membrane–cytoskeletal interactions: Specific association of integrin and talin arises in vivo after phorbol ester treatment of peripheral blood lymphocytes, Proc. Natl. Acad. Sci. USA 85:497–501 (1988).

*Primary Examiner*—Christina Y. Chan
*Attorney, Agent, or Firm*—Campbell and Flores

[57] ABSTRACT

Antibodies against integrins are disclosed, as are methods of making same. Such antibodies are elicited by immunizing with synthetic peptides corresponding to the cytoplasmic domains, or functional portions thereof, of various integrin subunits. Peptides employed for such immunization include known cytoplasmic domain amino acid sequences for integrin subunits, as well as newly discovered cytoplasmic domain amino acid sequences for integrin subunits. The latter amino acid sequences are also disclosed and described herein.

3 Claims, 3 Drawing Sheets

FIG. 3

PEPTIDES OF THE CYTOPLASMIC DOMAIN OF INTEGRIN

This application is a continuation of U.S. application Ser. No. 07/973,547, filed Nov. 9, 1992, now abandoned, which is a continuation of U.S. application Ser. No. 07/357,024, filed May 25, 1989, now abandoned.

BACKGROUND OF THE INVENTION

Integrins are a family of adhesion receptors (reviewed in Ruoslahti and Pierschbacher, Science, 238:491–497, 1987). An integrin molecule is a heterodimeric membrane protein composed of one α subunit and one β subunit. Several subunits of each kind are known, and various combinations of these subunits make up receptors with different ligand specificities. The ligands for integrins are extracellular matrix proteins such as fibronectin, laminin, collagens and vitronectin or membrane proteins at the surface of other cells.

By binding to their ligands, integrins mediate the adhesion of cells to extracellular matrices and other cells. Adhesion is important for a cell. It provides anchorage, traction for migration, signals for homing, and regulates growth and differentiation of cells.

There are a number of instances where it is important to determine the complement of adhesion receptors possessed by cells. For example, it has been shown that inhibition of the fibronectin receptor function by synthetic peptides that bind to this receptor prevents tumor cells (Gehlsen et al., J. Cell. Biol., 106:925–930, 1988) or lymphocytes (Thiery et al., Ann. Rev. Cell. Biol., 1:91–113, 1985) from invading and migrating through tissues. In contrast, inhibition of the function of another integrin, the vitronectin receptor, has no effect on tumor cell migration (Gehlsen et al., op cit.). Thus, it would be important to determine whether a tumor has fibronectin receptors to assess the potential susceptibility of its invasive properties to inhibitors of this receptor. Similar considerations apply to the laminin receptors, which are also thought to play a role in invasion (Gehlsen et al., Science 241:1228–1229, 1988).

Another situation in which determination of the integrins possessed by cells is important, is when the tissue of origin of a tumor is analyzed. Tissue-specific markers have proven to be a very useful adjunct for such an analysis in the clinical pathology setting. Some of the integrins are tissue-specific in their expression, providing potentially useful markers for the diagnosis of tumor origin. Thus, for example, the primary platelet integrin gp IIb/IIIa is restricted to platelets and leukemia cells capable of expressing megakaryocytic properties (in BIOCHEMISTRY OF PLATELETS, D. R. Phillips and M. A. Schuman, Eds., Academic Press, N.Y., 1986; Suzuki et al., J. Biol. Chem. 262:14080–14085, 1987). As is the case with most other cellular markers, the detection of integrins in cells and tissues is best accomplished with antibodies.

There thus exists a need for antibodies specific to various integrins. This invention satisfies this need by providing a simple and reproducible method for the preparation of anti-integrin antibodies suitable for the detection and quantitation of integrins by immunoassays.

SUMMARY OF THE INVENTION

The present invention provides anti-integrin antibodies produced by immunizing with peptides derived from the cytoplasmic domains of integrin subunits. The α and β integrin subunits each have a short cytoplasmic tail that can be entirely, or in part, reproduced as synthetic peptides. Particular peptide sequences useful for such immunization, including a variant $\beta_3$' peptide, are also provided.

BRIEF DESCRIPTION OF DRAWINGS

FIG. 3 shows the cDNA sequence and deduced amino acid sequence of the cytoplasmic domain of the $\beta_3$' subunit. The sequence of the EcoR1 fragment containing the alternative cytoplasmic domain is shown and referred to as $\beta_3$'. Part of the published $\beta_3$ sequence is shown for comparison. Amino acids are indicated in single-letter code. The putative transmembrane domain in the $\beta_3$ sequence is boxed. The site where the two sequences become different is indicated by an arrow. Polyadenylation signals are underlined.

DETAILED DESCRIPTION OF THE INVENTION

Figure 1:
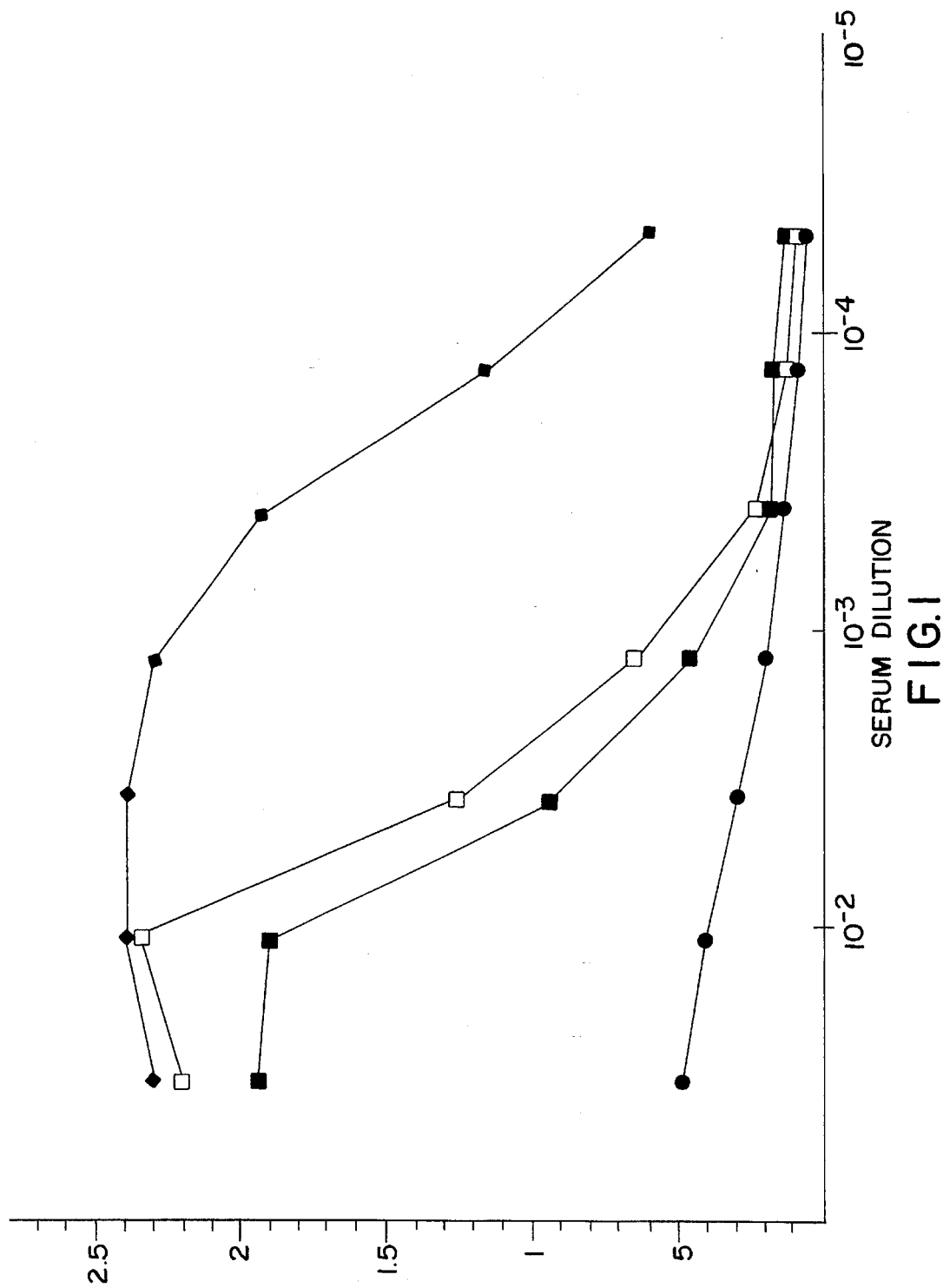
FIG. 1 shows the reactivity of antisera prepared against the cytoplasmic domains of the $\alpha_5$ and $\beta_1$ subunit with the fibronectin receptor ($\alpha_5\beta_1$) in ELISA. Microtiter wells were coated by incubation with purified human placental fibronectin receptor (10 μg/ml in Tris buffered saline, pH 7.4, containing 5 mM β-octylglucopyranoside). Residual binding sites on the plastic were saturated by post-coating with phosphate buffered saline containing 0.25% BSA. The wells were then incubated with the indicated dilutions of the following sera: (●) preimmune serum, (■) antiserum against $\beta_1$ cytoplasmic peptide (after second injection of the antigen), (□) antiserum against $\beta_1$ cytoplasmic peptide (after third injection of the antigen), (◆) antiserum against $\alpha_5$ cytoplasmic peptide (after the fourth injection of the antigen). Bound antibodies were detected with alkaline phosphatase conjugated goat anti-rabbit IgG (Cappel Laboratories, Malvern, Pa.). The color reaction was quantitated by light absorbance at 600 nM.

The present invention relates to antibodies prepared against integrins. These antibodies are characterized by their having been elicited by immunizing with synthetic peptides corresponding to the cytoplasmic domains or portions thereof of various integrin subunits. The amino acid sequences of several integrin subunits are available (Tamkun et al., Cell 42:271–282, 1986; Argraves et al., J. Cell Biol. 105:1183–1190, 1987; Suzuki et al., J. Biol. Chem. 262:14080–14085, 1987; Poncz et al., J. Biol. Chem. 262:8476–8482, 1987; Fitzgerald et al., J. Biol. Chem. 262:3936–3939, 1987; Fitzgerald et al., Biochemistry 26:8158–8165, 1987; DeSimone and Hynes, J. Biol. Chem. 263:5333–5340, 1988; Kishimoto et al., Cell 48:681–690, 1987; Law et al., EMBO J. 6:915–919, 1987; Pytela, R., EMBO J. 7:1371–1378, 1988 all of which are incorporated herein by reference).

Immunization with such peptides has two distinct advantages: the immunization is performed with a synthetic peptide corresponding to the end of the natural polypeptide, and the synthetic peptide corresponds to an intracellular peptide domain. Peptides from either end of a protein have been found to be more likely to be immunogenic than ones derived from internal sequences in the same protein (Harlow and Lane, ANTIBODIES: A LABORATORY MANUAL, Cold Spring Harbor, 1988) and it was felt that antibody production to intracellular proteins (or cytoplasmic portions of transmembrane proteins) is less likely to be hampered by tolerance than production of antibodies to proteins that exist extracellularly. For these reasons, and because the various integrin subunits differ in their cytoplasmic sequences, peptides from the cytoplasmic domains were considered good candidates for use as immunogens in the production of antibodies against integrins. However, the results were unexpectedly good in that unusually potent antisera reactive with the appropriate integrin were obtained in each case.

The peptides listed in Table I, which are based on known cytoplasmic domain amino acid sequences from integrin subunits, were synthesized using the Applied Biosystems, Inc. model 430A automatic peptide synthesizer and the chemistry provided by the manufacturer. In some cases the peptide was synthesized with a cysteine added at the $NH_2$-terminus to facilitate coupling to carrier protein. The cysteine-containing peptides were coupled to keyhole limpet hemocyanin (KLH) by using m-maleimidobenzoyl-N-hydroxysuccinimide ester (Pierce Chemical Co., Rockford, Ill.) according to O'Sullivan et al. (Analyt. Biochem. 100::100–108, 1979) which is incorporated herein by reference. The peptides with no added cysteine were similarly coupled to KLH by using N-succinimidyl 3-(2-pyridyldithio) propionate (Pharmacia Fine Chemicals, Piscataway, N.J.) according to the manufacturer's instructions. The resulting conjugates were emulsified in Freund's complete adjuvant and injected into rabbits. Further injections of conjugate in Freund's incomplete adjuvant were given after one, two and three months. The dose of each injection was equivalent to 0.6 mg of peptide. Blood was collected 10 days after the third and fourth injection. The antisera were tested against the glutaraldehyde-cross linked peptides and isolated receptors in ELISA (Engvall, Meth. Enzymol. 70:419–439, 1980), in immunoprecipitation and immunoblotting, and by staining cells in immunofluorescence, as is well known in the art. The results show that the antisera specific for the individual integrins have been obtained.

EXAMPLE I

Identification of a novel cytoplasmic sequence for integrin subunit $\beta_3$

A CDNA clone that encodes a $\beta_3$ variant, termed $\beta_3$', with a new cytoplasmic domain sequence was identified. This cytoplasmic domain was used to generate one of the antisera of this invention. cDNA clones were isolated from λgt 11 cDNA libraries made from myeloma cell RNA by use of a cDNA cloning kit (Amersham, Arlington, Ill.) and from placental RNA (Millan, J. Biol. Chem. 261:3112–3115 1986). A 21-mer oligonucleotide, 5' CAC TGA GAG CAG GAC CAC CAG 3', from the published sequence of $\beta_3$ (Rosa et al., Blood 72:593–600, 1988 and Fitzgerald et al., Supra) or inserts from cDNA clones were used for the screening.

Screening of $3 \times 10^5$ plaques from a M 21 myeloma cDNA library with a 21-mer oligonucleotide probe from the published $\beta_3$ cDNA sequence revealed one positive clone. The 1.3 kb cDNA insert from this clone was used to screen $7 \times 10^5$ plaques from a placental λgt 11 cDNA library, resulting in the isolation of three positive clones. The inserts of the isolated cDNA clones were subcloned into the phage vector M13 mp19 as is well known in the art and sequenced by the dideoxy chain termination method either manually with dATP 5'-α-[$^{35}$S] thiotriphosphate as the label or by using an automated DNA-sequencer and fluorescent primers (Applied Biosystems, Foster City, Calif.; model 370A) according to the manufacturer's instructions.

Figure 3:
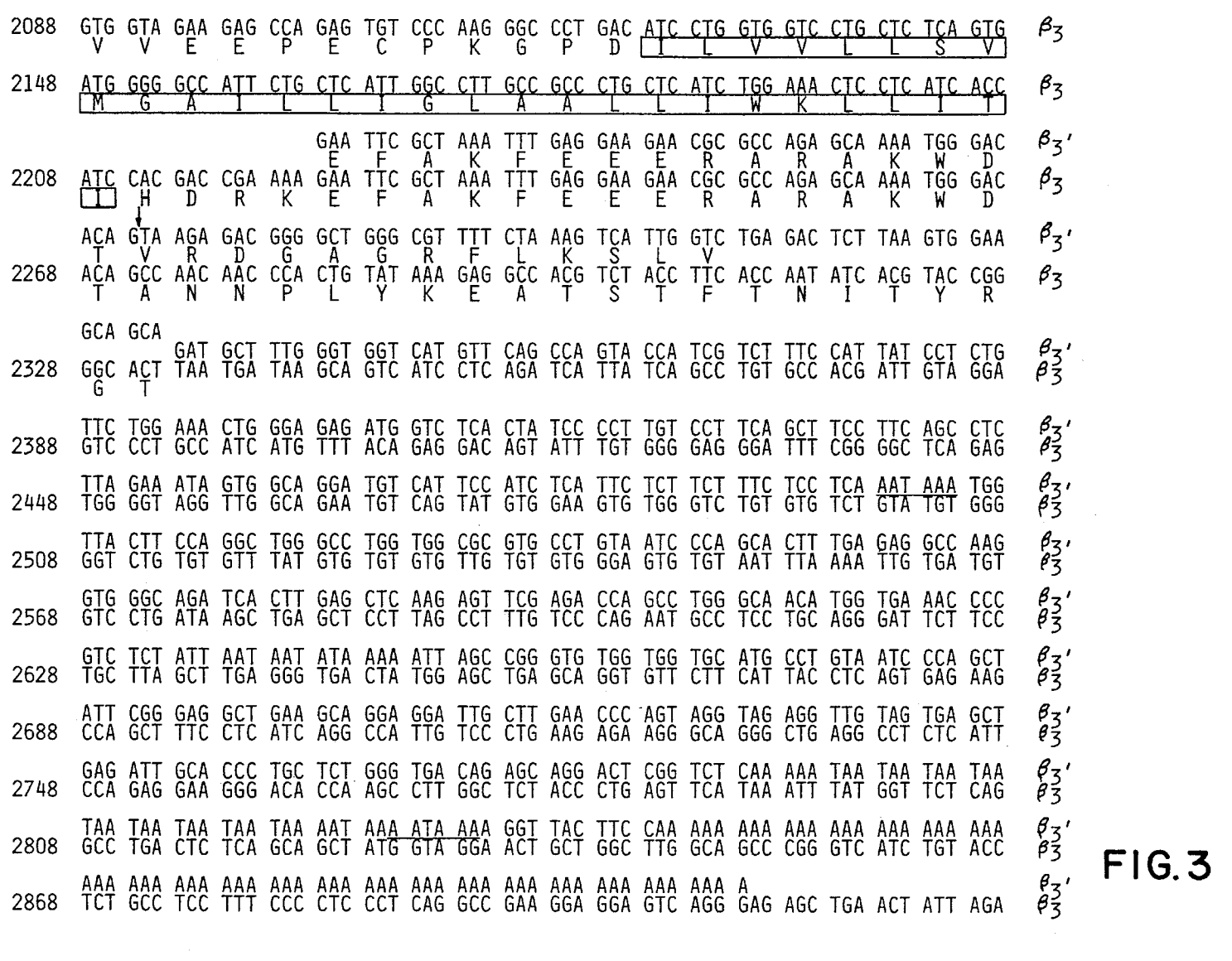

Partial sequences of two of the clones revealed the same sequence as in the published $\beta_3$ sequence. Unexpectedly, the third clone (#10) was different. This 1.8 kb clone consisted of 1.0 and 0.8 kb EcoR1 fragments, and its 5' end is in the extracellular domain (base number 1254; sequence numbers are according to Rosa et al., Blood 72:593–600 (1988). The published $\beta_3$ sequence and the clone 10 sequence were found to be identical through the 5' fragment and part of the 3' fragment but diverged within the 3' fragment in the region that encodes the cytoplasmic domain of the $\beta_3$ polypeptide. The DNA sequence of the 3' fragment and the amino acid sequence derived from it are shown in FIG. 3. The variant sequence encodes a cytoplasmic domain in which the COOH-terminal 21 amino acids of the previously known $\beta_3$ sequence have been replaced with a new 13-amino acid sequence. (See Table 1.) The identity of most of the $\beta_3$' cDNA sequence with the known $\beta_3$ sequence and the fact

TABLE I

| | $NH_2$ | COOH |
|---|---|---|
| Known sequences: | | |
| $\beta_1$ | | EFAKFEKEKMNAKWDTGENPIYKSAVTTVVNPKYEGK |
| $\beta_3$ | | KFEEERARAKWDTANNPLYKEATSTFTNITYRGT |
| $\alpha_5$ | | CEKAQZLKPPATSDA |
| $\alpha_v$ | | KRVRPPQEEQEREQLQPHENGEGNSET |
| Sequences of current invention: | | |
| $\beta_3$' 4–29 subsequence | | KFEEERARAKWDTVRDGAGRFLKSLV |
| | | or an immunological subsequence thereof |
| $\beta_3$' 13–29 subsequence | | KWDTVRDGAGRFLKSLV |
| $\beta_3$' 17–29 subsequence | | VRDGAGRFLKSLV |

Amino acids are designated by their standard one letter abbreviation.

that these two sequences diverge near the usual splice site dinucleotide GT provide a strong indication that the $\beta_3$ and $\beta_3$' mRNAs arise from the same gene by alternative splicing.

The existence of a cDNA clone containing the $\beta_3'$ suggests that the $\beta_3'$ is expressed at least at the mRNA level. Further proof for the existence of such a cDNA was obtained by applying the reverse transcriptase-polymerase chain reaction method (RT-PCR, Rappolee et al., Science 241:708–712 (1988) which is incorporated herein by reference). RNA was isolated from MG-63 human osteosarcoma cells (American Type Culture Collection) and from human placental tissue by using the guanidine isothiocyanate method and used to generate DNA fragments from $\beta_3$ and $\beta_3'$ mRNA by RT-PCR.

RT-PCR was essentially done as described Rappolee, Supra. Total RNA (0.4 μg) was reverse transcribed using 200 U of Moloney murine leukemia virus reverse transcriptase (Bethesda Research Laboratories, Gaithersburg, Md.), 0.4 μg oligo p(dT) 12–18 and 2 μg nuclease-free bovine serum albumin. The total volume was 20 μl. One-tenth of the resulting cDNA was amplified by using the DNA amplification reagent kit and thermal cycler (Perkin-Elmer Cetus, Norwalk, Conn.). One unit of Taq polymerase and 1 μM of each primer were used; the final volume was 50 μl. The following primers were used: #1—extracellular domain 1851–1875; #2—extracellular domain 1879–1903; #3—extracellular domain 2064–2088; #4—cytoplasmic domain $\beta_3$ 2273–2297; #5—3' untranslated region $\beta_3$ 2559–2583; #6—3' untranslated region $\beta_3$ 3104–3128; #7—3' untranslated region $\beta$ 3472–3497; #8—cytoplasmic domain+3' untranslated region alternative sequence 2301'–2331' (the ' symbol refers to the variant $\beta$ sequence); #9—3' untranslated region alternative sequence 2408'–2432'. Of the PCR mixture, 15 μl were electrophoretically separated in 2% agarose gels or 3% Nu Sieve™ brand GTG agarose gel/1% SaeKem™ brand GTG agarose gel (FMC, Rockland, Me.) and DNA was visualized using ethidium bromide. Hae III fragments of ΦX174 RF DNA (500 ng) were used as molecular size markers (Bethesda Research Laboratories, Gaithersburg, Md.). RNA digestion was performed using 50 μg ribonuclease A (Sigma, St. Louis, Mo.) and 14 μg total RNA in a total volume of 30 μ. Digestion was for 20 hours at 37° C.

Analysis of the DNA fragments generated by the RT-PCR showed that a fragment of the expected size was obtained in each case both when the primers came from the $\beta_3$ sequence and when they came from the $\beta_3'$ sequence. Controls showed that the production of these fragments in the reaction was sensitive to digestion of the template MG-63 cell and placental RNA with RNAse prior to the RT-PCR. These results show that the $\beta_3'$ mRNA is expressed in the MG-63 cells and in the placenta. To provide a reagent for the detection of $\beta_3'$ at the protein level, a peptide was made from the cytoplasmic tail of $\beta_3'$ (Table 1) and used to generate an antiserum.

EXAMPLE II

Reactivity of anti-integrin antisera in ELISA

A total of 5 antisera were prepared against the cytoplasmic domains of 5 different integrin subunits. Each immunization yielded an antiserum reactive with the immunizing peptide. All antisera were also reactive with the receptor proteins from which the peptide sequence was taken when tested in ELISA against the receptor. The $\beta_3'$ antiserum reacted also with the $\beta_3$ peptide which shares the sequence KWDT with the $\beta_3'$ peptide. It could be made specific for the $\beta_3'$ peptide by absorption with the $\beta_3$ peptide coupled to cyanogen bromide-activated Sepharose™ brand beaded agarose matrix (Pharmacia). After the absorption, the antiserum reacted only with the $\beta_3'$ peptide. It continued to react with the isolated vitronectin receptor suggesting that this receptor contains molecules with the $\beta_3'$ sequence in addition to those representing $\beta_3$.

FIG. 1 shows an example of an ELISA titration curve with a number of bleedings from rabbits immunized with the cytoplasmic domains of the $\alpha_5$ and $\beta_1$ integrin subunits. It can be seen that specific reactivity against the purified intact receptor is present in each of the bleedings taken after the immunization, and that the amount of the antibody in the antiserum increases (as indicated by the highest dilution that shows binding of the receptor) as the immunization progresses.

Figure 2:
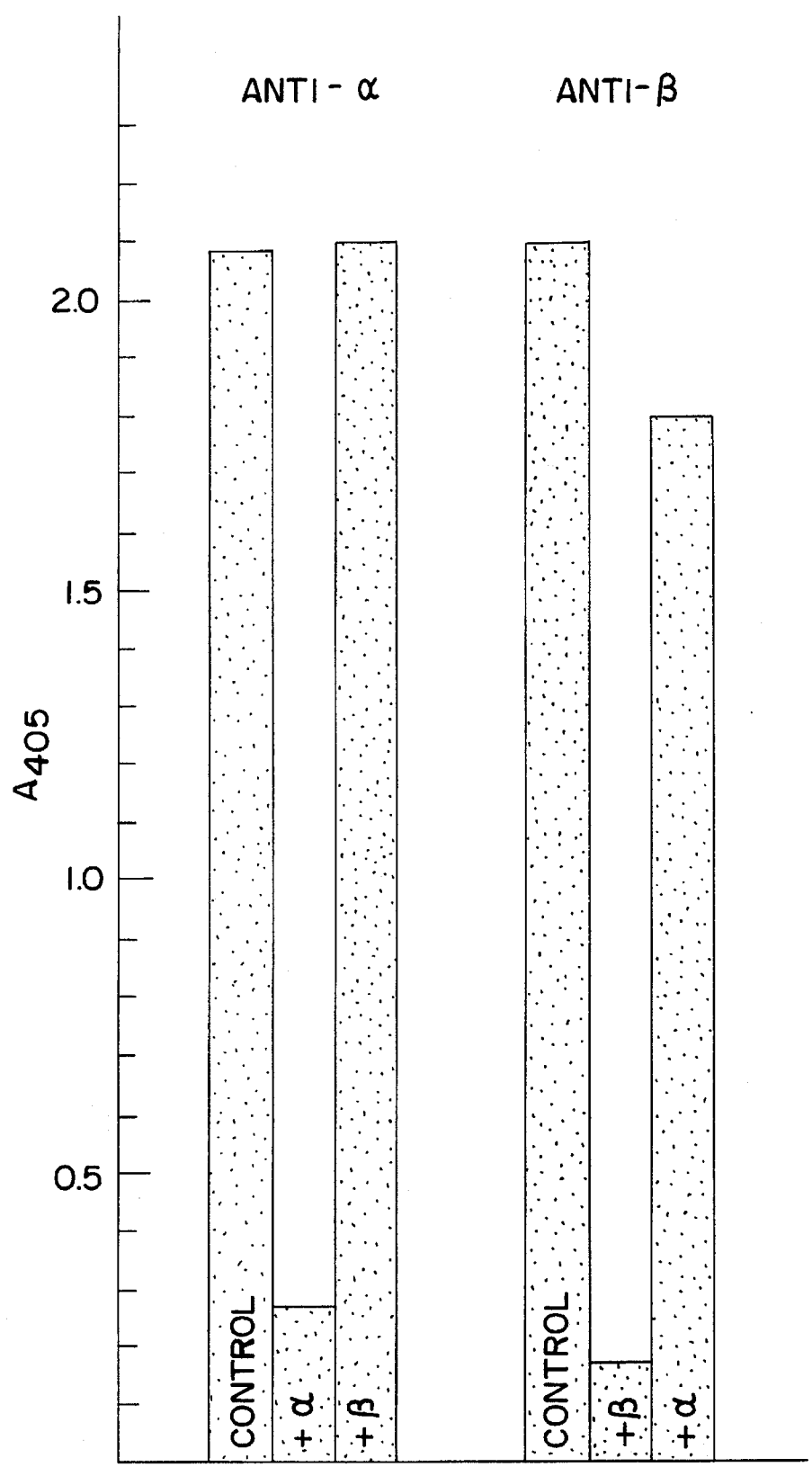
FIG. 2 demonstrates the specificity of cytoplasmic domain antisera by peptide inhibition in ELISA. Microtiter wells were coated with a solution containing 3 μg/ml of purified vitronectin receptor. Antisera prepared against peptides from the cytoplasmic domains of the vitronectin receptor α and β subunits diluted 1:1000 were incubated in the wells without added peptide (control) or with the indicated peptide at a concentration of 10 μg/ml. The binding of the antibodies to the wells was detected with alkaline phosphatase-conjugated anti-rabbit IgG (Cappel Laboratories, Malvern, Pa.).

FIG. 2 shows an example of the specificity of the cytoplasmic domain antisera. In this case antisera to the vitronectin receptor $\alpha$ and $\beta$ subunits ($\alpha_v$ and $\beta_3$ in the nomenclature proposed by Hynes (Cell 48:549–554, 1987) were allowed to bind to wells coated with the vitronectin receptor and inhibition of the binding by peptides was studied. The results show that the binding of the anti-$\alpha_v$ subunit antiserum to the receptor was inhibited by the immunizing ($\alpha_v$) peptide but not by the peptide that came from the $\beta_3$ subunit. The opposite was true of the anti-$\beta_3$ subunit antiserum.

EXAMPLE III

Specificity of anti-integrin antisera in immunoblotting and immunoprecipitation

Immunoblotting showed that the anti-cytoplasmic peptide antisera bound to the integrin subunit from which the immunizing peptide was derived from.

The antisera were also reactive with integrins in solution as shown by immunoprecipitation. SDS-polyacrylamide gel electrophoresis analysis of material immunoprecipitated from surface-iodinated (Lebien et al., J. Immunol. 129:2287–2292, 1987 incorporated herein by reference) Chinese hamster ovary (CHO) cells (Urlaub and Chasin, Proc. Natl. Acad. Sci., USA 77:4216–4220, 1980) by antisera against the $\alpha_5$ and $\beta_1$ integrin subunits revealed two radioactive polypeptides the mobility of which corresponded to the $\alpha_5$ and $\beta_1$ subunits. No other detectable bands were present. Normal rabbit serum did not precipitate detectable bands. These results show that the antisera specifically recognize the appropriate integrin among all the various proteins that became labeled in the CHO cells.

EXAMPLE IV

Detection of receptors in cells by immunofluorescence

The anti-cytoplasmic domain antisera can be used to detect the presence of integrins in cell membranes. For example, an antiserum prepared against the $\alpha_5$ and $\beta_1$ subunit cytoplasmic domains was used to stain cultured CHO cells by immunofluorescence. Patchy staining was seen with both antisera, indicating that both subunits are present in the CHO cells and that the integrins containing these subunits are localized in specialized adhesion structures at the cell surface. The immunizing peptide inhibits the staining and no staining was obtained with preimmune control sera.

Although the invention has been described with reference to the presently-preferred embodiments, it should be understood that various modifications can be made without departing from the spirit of the invention. Accordingly, the invention is limited only by the following claims.

We claim:

1. A peptide consisting of the amino acid sequence of the cytoplasmic domain of integrin subunit $\beta_3$', KFEEERAR AKWDTVRDGAGRFLKSLV.

2. A peptide consisting of the sequence KWDTVRDGAGRFLKSLV.

3. A peptide consisting of the sequence VRDGAGRFLKSLV.

* * * * *

UNITED STATES PATENT AND TRADEMARK OFFICE
CERTIFICATE OF CORRECTION

PATENT NO.   : 5,498,694
DATED        : March 12, 1996
INVENTOR(S)  : Erkki I. Ruoslahti It is certified that error appears in the above-indentified patent and that said Letters Patent is hereby corrected as shown below:

In column 5, line 12, please delete "described Rappolee" and replace therefor with --described by Rappolee--.

In column 5, line 39, please delete "30 $\mu$" and replace therefor with --30 $\mu$l--.

Signed and Sealed this

Eighth Day of December, 1998

Attest:

BRUCE LEHMAN

Attesting Officer

Commissioner of Patents and Trademarks